(12) United States Patent
Galibert et al.

(10) Patent No.: US 10,017,783 B2
(45) Date of Patent: Jul. 10, 2018

(54) BACULOVIRUS SYSTEM FOR THE EXPRESSION OF A GENE THERAPY VECTOR

(75) Inventors: Lionel Galibert, Levallois-Perret (FR); Otto-Wilhelm Merten, Crespières (FR); Aurélien Jacob, Montrouge (FR)

(73) Assignee: GENETHON, Evry (FR)

( * ) Notice: Subject to any disclaimer, the term of this patent is extended or adjusted under 35 U.S.C. 154(b) by 0 days.

(21) Appl. No.: 14/234,988

(22) PCT Filed: Jul. 27, 2012

(86) PCT No.: PCT/FR2012/051791
§ 371 (c)(1),
(2), (4) Date: Jun. 23, 2014

(87) PCT Pub. No.: WO2013/014400
PCT Pub. Date: Jan. 31, 2013

(65) Prior Publication Data
US 2014/0349374 A1 Nov. 27, 2014

(30) Foreign Application Priority Data
Jul. 27, 2011 (FR) ..................................... 11 56878

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2710/14044* (2013.01); *C12N 2750/14043* (2013.01); *C12N 2750/14141* (2013.01); *C12N 2750/14151* (2013.01); *C12N 2800/50* (2013.01); *C12N 2830/20* (2013.01); *C12N 2999/007* (2013.01)

(58) Field of Classification Search
None
See application file for complete search history.

(56) References Cited

FOREIGN PATENT DOCUMENTS

| EP | 2 133 428 A1 | * | 12/2009 |
|----|----|----|----|
| WO | WO 2004/022760 | * | 3/2004 |
| WO | WO 2004/022760 A1 | | 3/2004 |
| WO | WO 2008/099148 A1 | | 8/2008 |
| WO | WO 2011/020710 | * | 2/2011 |

OTHER PUBLICATIONS

Noad et al., BMC Molecular Biology 2009, 10:87, 1-13.*
Chaabihi et al., Journal of Virology, 1993, 67(5):2664-2671.*
Kaba et al., Journal of Virological Methods, 2004, 122:113-118.*
L. Gailbert et al., "Baculovirus Deleted for Chitinase, Cathepsin and p10 Genes Improves Purified rAAV8 Quality." Wageningen UR Publication, 2006.
R. H. Smith et al., "A Simplified Baculovirus-AAV Expression Vector System Coupled with One-Step Affinity Purification Yields High-Titer rAAV Stocks From Insect Cells." Molecular Therapy, vol. 17, No. 11, pp. 1888-1896, 2009.
G. Aslanidi et al., "An Inducible System for Highly Efficient Production of Recombinant Adeno-Associated Virus (rAAV) Vectors in Insect sf9 Cells." PNAS, vol. 106, No. 13, pp. 5059-5064, Mar. 31, 2009.
R. J. Noad et al., "Multigene Expression of Protein Complexes by Iterative Modification of Genomic Bacmid DNA." BMC Molecular Biology, vol. 10:87, pp. 1-13, 2009.
C. Wang, "Hybrid Baculovirus-Adeno Associated Virus Vectors for Prolonged Transgene Expression in Human Neural Cells." Journal of NeuroVirology, vol. 14, pp. 563-568, 2008.
J. T. Gray et al., "Design and Construction of Functional AAV Vectors." Adeno-Associated Virus: Methods and Protocols, Methods in Molecular Biology, vol. 807, pp. 25-46, 2011.

* cited by examiner

*Primary Examiner* — Nicole Kinsey White
(74) *Attorney, Agent, or Firm* — Saliwanchik, Lloyd & Eisenschenk

(57) ABSTRACT

The invention relates to a recombinant baculoviral genome useful for the production of viral vectors for gene therapy, allowing said production from a single infection.

14 Claims, 6 Drawing Sheets

BACULOVIRUS SYSTEM FOR THE EXPRESSION OF A GENE THERAPY VECTOR

Figure 1:
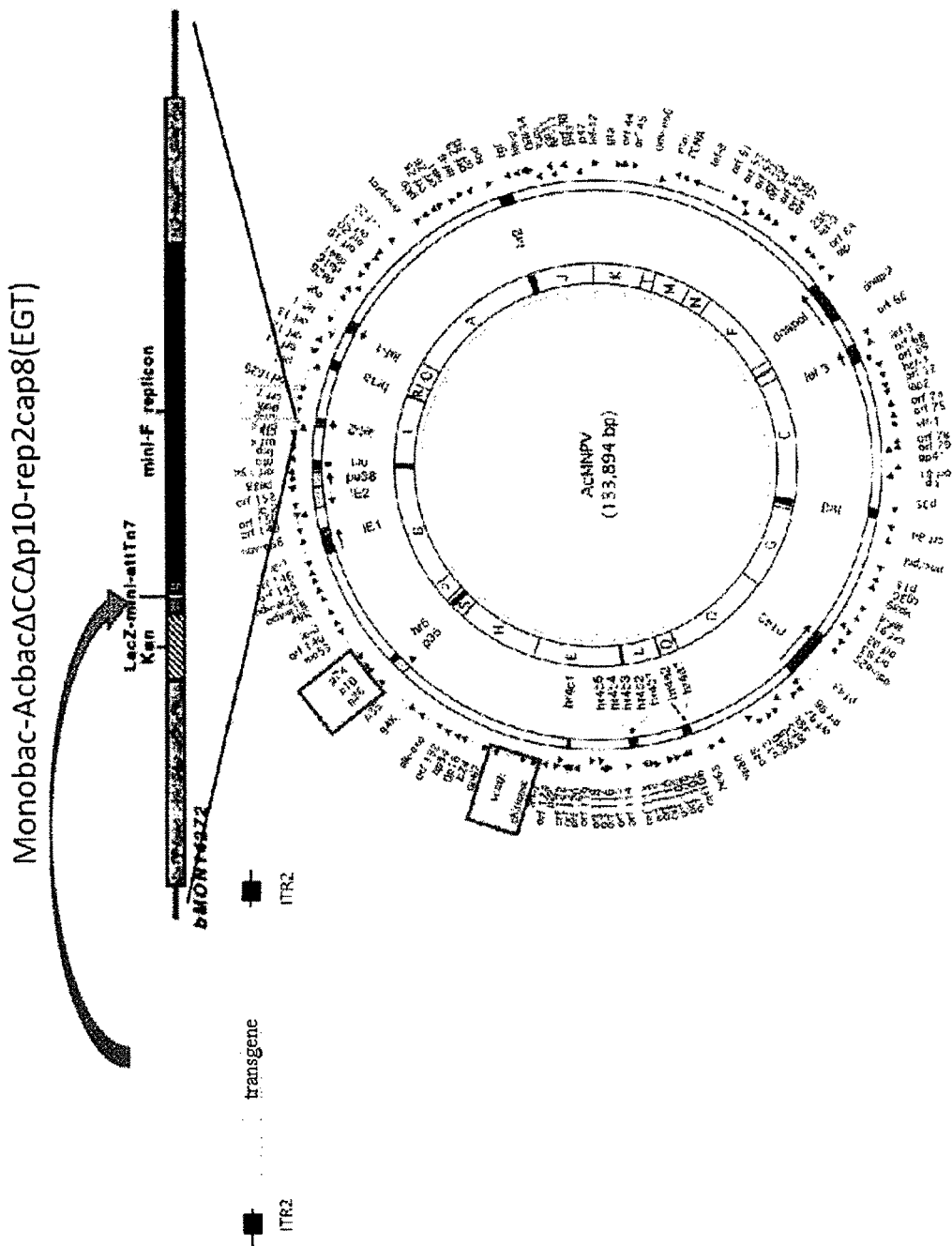

Recombinant adeno-associated viruses (or rAAVs) are currently considered to be the most promising viral vectors in gene therapy. However, their large-scale production remains a limiting factor for the development of therapies of this type. Production systems which exploit the capacity of baculoviruses to infect insect cells have thus been developed with a view to overcoming this problem, and for biosafety reasons (Urabe et al. 2002; Hum. Gene Ther. 13: 1935-1943; US 20030148506; US 20040197895). According to the protocol initially proposed, infection of insect cells with 3 different baculoviruses was required in order to provide the rep and cap helper genes and the construct comprising the recombinant AAV vector containing the transgene required to form the recombinant viral particle. A simplification of this system consists of the integration of the rep and cap genes into a single baculovirus resulting in a production system using 2 baculoviruses (rep/cap bac and transgene-bac) (Smith et al. 2009; Mol. Ther. 17: 1888-1896). Moreover, the group of Sergei Zolotukhin (Aslanidi et al. 2009; Proc. Natl. Acad. Sci. USA 206: 5059-5064 and WO 2010/114948) has recently developed Sf9 cell lines stably transformed with the rep and cap genes. With such a cell line, infection with a single baculovirus (comprising in its genome the therapeutic gene of interest flanked by ITR of an AAV) would make it possible to obtain a recombinant AAV. However, this system has several drawbacks. Firstly, the generation of cell clones is fastidious and the clones obtained are often characterized by genetic instability which results in an exploitation window which is limited in time. In addition, a high frequency of packaging of foreign DNA which does not correspond to the vector of interest (sequences of rep and cap and of genes for resistance to an antibiotic) has been observed, thereby posing a considerable problem in terms of biosafety. Such clones are thus unsuitable for the production of batches of vectors intended for clinical use.

All the baculoviruses used in the studies mentioned above comprise the insertion of the gene of interest (whether it is the rep and/or cap genes or the therapeutic gene of interest) into the polyhedrin cloning site of the baculovirus genome. This site is conventionally chosen owing to the high levels of expression which can be obtained from this locus. This site is also used in the system developed by Luckow et al. (1993; J. Virol. 67:4566-4579) into which a bacterial origin of replication, a kanamycin resistance gene and a "Tn7" recombination cloning site are inserted. This system is known as a bacmid. However, the use of this sole locus constitutes a limiting factor, in particular if it is desired to be able to express several heterologous sequences from a single baculovirus. It is in this context that Noad et al. (2009) compared the conventional locus—polyhedrin (Tn7 of the bacmid, present at the polyhedrin site)—with various potential cloning sites and identified 7 additional loci (ctx, egt, 39k, orf51, pg37, iap2, odv-e56) in the genome of AcMNPV allowing strong expression of heterologous genes (Noad et al. 2009; BMC Molecular Biology 10: 87; WO 2010/055292). It was also shown that various genes cloned in several of these loci can be expressed concomitantly from the same genome. However, Noad et al. did not show whether these alternative loci were effective for the production of recombinant AAV or any other recombinant viral vector, which was not obvious given the complexity of these viral vectors and the major difficulties conventionally encountered during the production thereof.

SUMMARY OF THE INVENTION

Surprisingly, it has been possible to show that recombinant AAVs can be produced by virtue of a single baculovirus.

The invention thus relates to a recombinant baculovirus genome comprising heterologous sequences encoding all the components required for the production of a heterologous viral vector (i.e. the protein components of the vector and its genome) inserted into loci selected from the group consisting of the nonessential genes of the baculovirus which can be replaced with a sequence of interest without modifying the functioning of the baculovirus.

The invention in particular relates to a recombinant baculovirus genome comprising one or more expression cassettes for the protein components required for the production of a heterologous viral vector, and a recombinant genome of a heterologous viral vector (also subsequently referred to as heterologous genome), said expression cassettes and said heterologous genome being inserted into one or more locus selected from the group consisting of the egt, polyhedrin, ctx, 39k, orf51, gp37, iap2 and odv-e56, p10 and p94 loci. The baculovirus genome can in particular comprise at least one expression cassette for the AAV rep and/or cap genes, inserted into said one or more locus. According to one variant, said rep and cap genes are contained in a single expression cassette, in particular in reverse orientation, said cassette being more particularly inserted into the egt locus. In one particular embodiment, the recombinant genome of a heterologous viral vector is an AAV recombinant genome inserted into a different locus of the locus or loci used for the AAV rep and cap genes, said heterologous genome being in particular inserted at the level of the polyhedrin locus.

The invention relates, moreover, to a recombinant baculovirus genome comprising one or more expression cassettes for the AAV rep and/or cap genes, said one or more expression cassettes being inserted into a locus selected from the group consisting of the egt, ctx, 39k, orf51, gp37, iap2, odv-e56, p10 and p94 loci of the baculovirus genome. This recombinant baculovirus genome also preferably contains an AAV recombinant genome in a locus selected from the polyhedrin, egt, ctx, 39k, orf51, gp37, iap2, odv-e56, p10 and p94 loci of the baculovirus genome, said AAV recombinant genome being inserted into a locus different than the locus or loci used for the AAV rep and cap genes.

The recombinant baculovirus genomes according to the invention can in particular be derived from the AcMNPV baculovirus. Moreover, the recombinant baculovirus genome of the invention can also have the characteristic of being deficient for the chitinase, cathepsin and p10 genes.

When the recombinant baculovirus genome according to the invention contains a heterologous recombinant virus genome, said heterologous genome may comprise a heterologous gene encoding a protein, an interfering RNA or an antisense RNA, which is in particular therapeutic (so as to allow the production of a viral gene therapy vector).

According to one particular embodiment, the recombinant baculovirus genome is a recombinant bacmid.

The invention also relates to a recombinant baculovirus, the genome of which is a recombinant baculovirus genome, in particular a bacmid, according to the invention.

Moreover, the invention relates to a method for producing a recombinant baculovirus, comprising culturing a prokaryotic cell containing the recombinant bacmid defined in the present application under conditions suitable for the production of a baculovirus.

The invention also provides a eukaryotic or prokaryotic cell containing the recombinant baculovirus genome disclosed, or infected with the recombinant baculovirus of the invention. Said cell may in particular be a mammalian cell (for example an HEK293 cell) or an insect cell derived from the *Spodoptera frugiperda* or *Trichoplusia ni* lines (for example, the Sf21, Sf9, TN 5B1-4 or High Five cells).

The invention also relates to a method for producing viral vectors, in particular viral gene therapy vectors. It is directed more particularly toward a method for producing a recombinant AAV, comprising culturing the recombinant baculovirus comprising the sequences required for the production of the protein or genetic components of an AAV, with a cell, in particular an insect cell (for example, an Sf9, Sf21, TN 5B1-4 or High Five cell), capable of being infected with said baculovirus, under conditions which allow the infection of the cell with the baculovirus and the production of said recombinant AAV.

FIGURE LEGENDS

FIG. 1. Monobac System for the production of rAAV vectors

The AcMNPV bacmid was inactivated for the chitinase, cathepsin and p10 genes. The expression cassette for the AAV rep2 and cap8 genes was inserted into the genome of the bacmid at the ecdysteroid UDP-glucosyltransferase (egt) locus, thus leaving the tn7 transposition site of the bacmid free for the insertion of the rAAV genome. A single baculovirus thus makes it possible to produce rAAV particles in insect cells.

Figure 2:
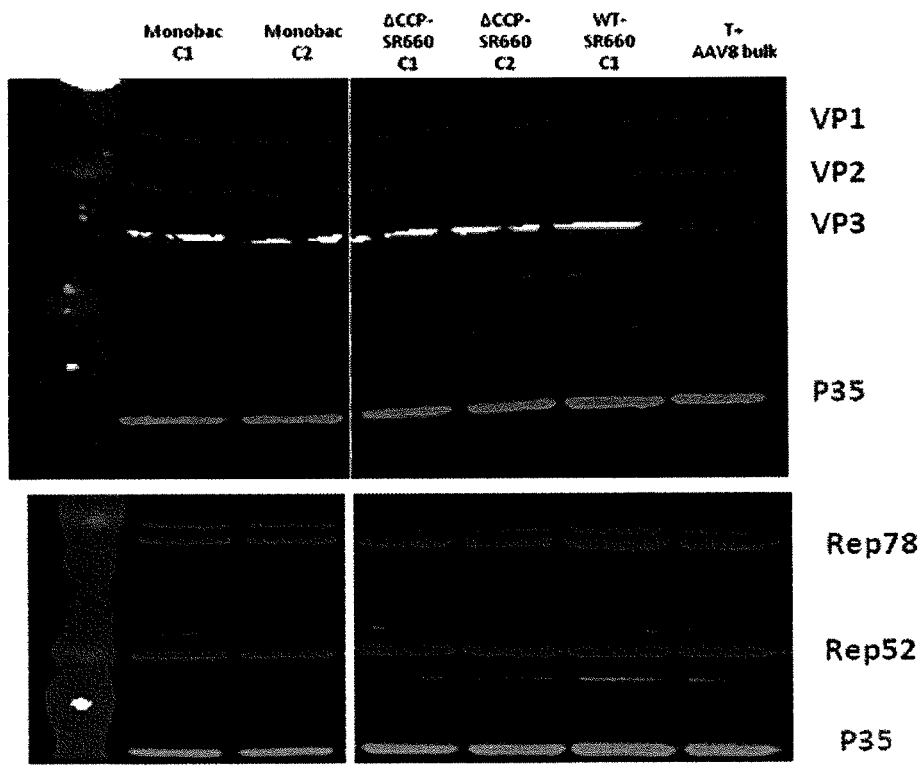

FIG. 2. Study of the locus effect for expression of the AAV rep2 and cap8 genes

The expression of the AAV Rep and Cap8 proteins was monitored by Western blot using baculoviruses expressing these proteins from the expression cassette inserted at the Tn7 site of the bacmid or at the egt locus, 3 days after infection of Sf9 cells. The protein expression standardization is monitored by measuring the expression of the P35 baculovirus protein.

Monobac C1 & C2: AcbacΔCCΔp10-rep2cap8(EGT).

ΔCCP-SR660 C1 & C2: AcbacΔCCΔp10-rep2cap8(Tn7).

WT-SR660 C1: AcbacWT.

T+ AAV8 bulk: positive control for AAV8-mSeAP production.

ΔCCΔp10: bacmid from which the cathepsin, chitinase and p10 genes have been deleted.

Acbac: bacmid derived from AcMNPV.

Figure 3:
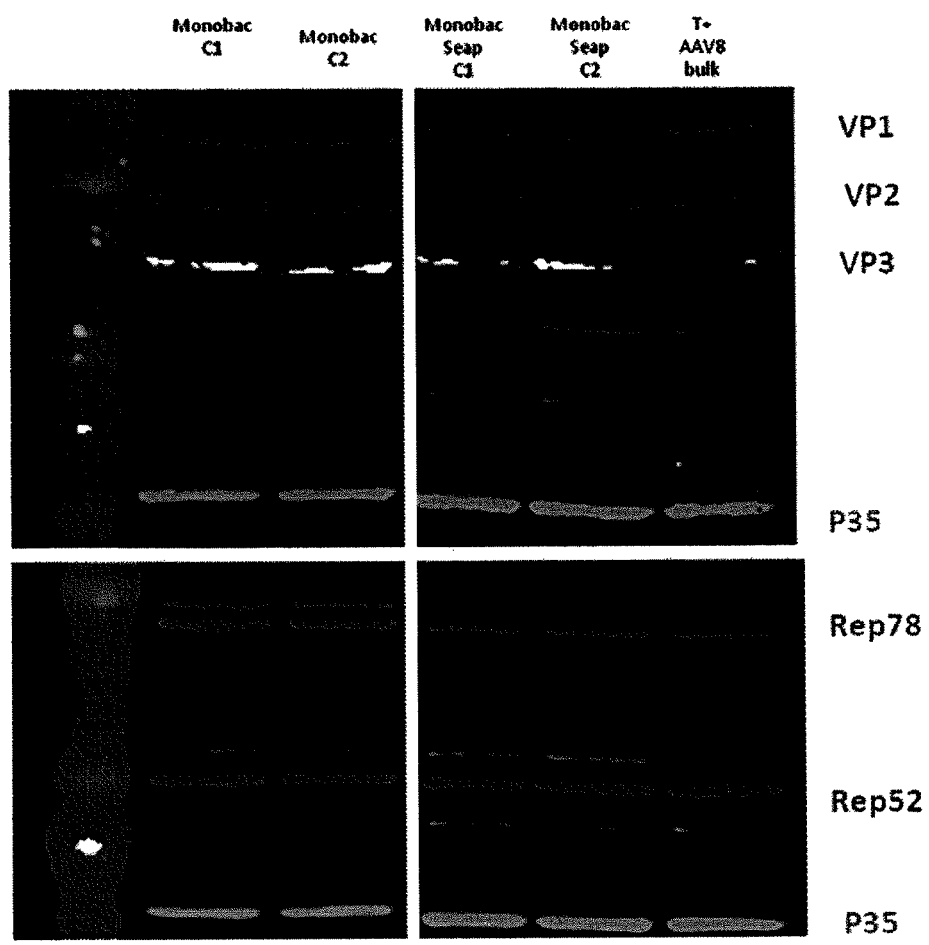

FIG. 3. Study of the locus effect for expression of the AAV rep2 and cap8 genes

The expression of the AAV Rep and Cap8 proteins was monitored by Western blot using baculoviruses expressing these proteins from the expression cassette inserted at the Tn7 site of the bacmid or at the egt locus, 3 days after infection of SD cells. The protein expression standardization was monitored by measuring the expression of the P35 baculovirus protein.

Monobac C1 and C2: AcbacΔCCΔp10-rep2cap8(EGT).

Monobac Seap C1 & C2: AcbacΔCCΔp10-rep2cap8 (EGT)-mSeAPTn7).

T+ AAV8 bulk: positive control for AAV8-mSeAP production.

Figure 4:
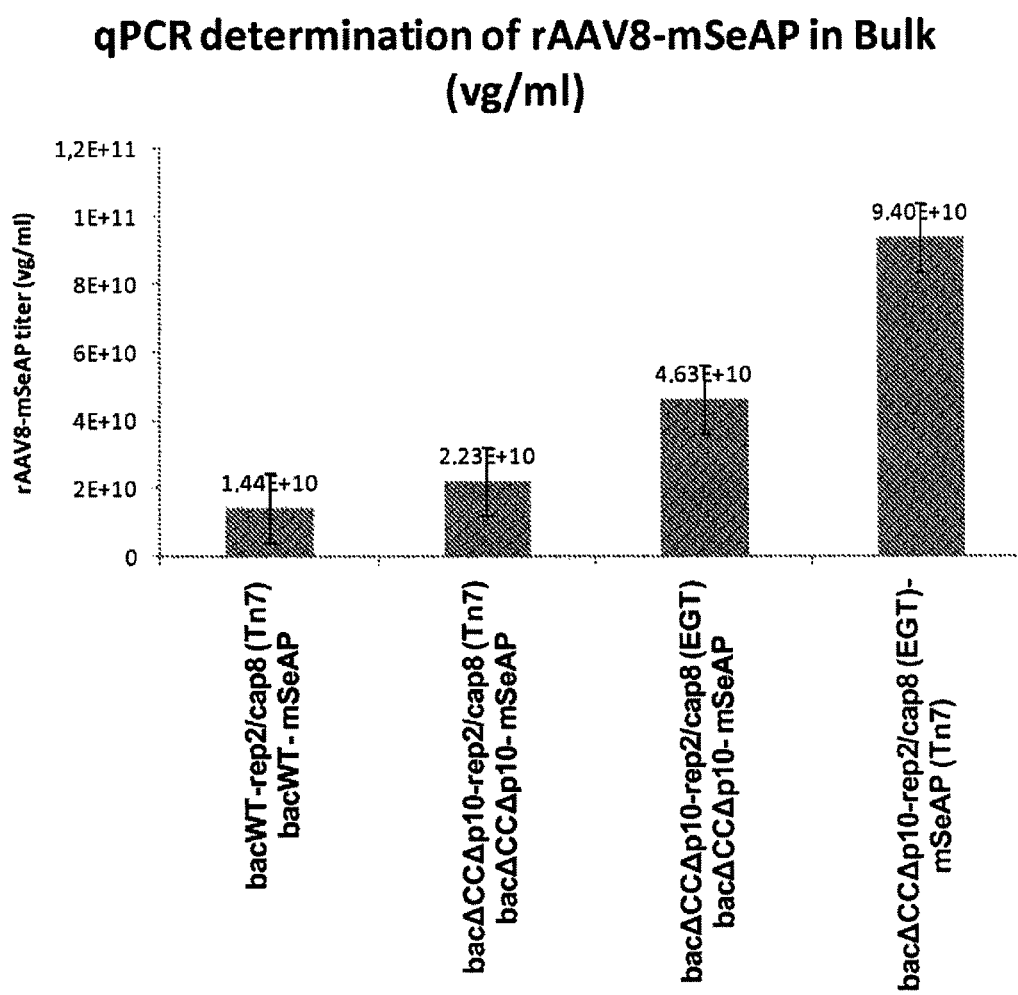

FIG. 4. rAAV productivity

The rAAV productivity in the monobac system was evaluated. The results are given as rAAV titer (vg/ml—vector genome/ml). 4 replicates were used per experiment, the error bar represents the standard deviation.

Figure 5:
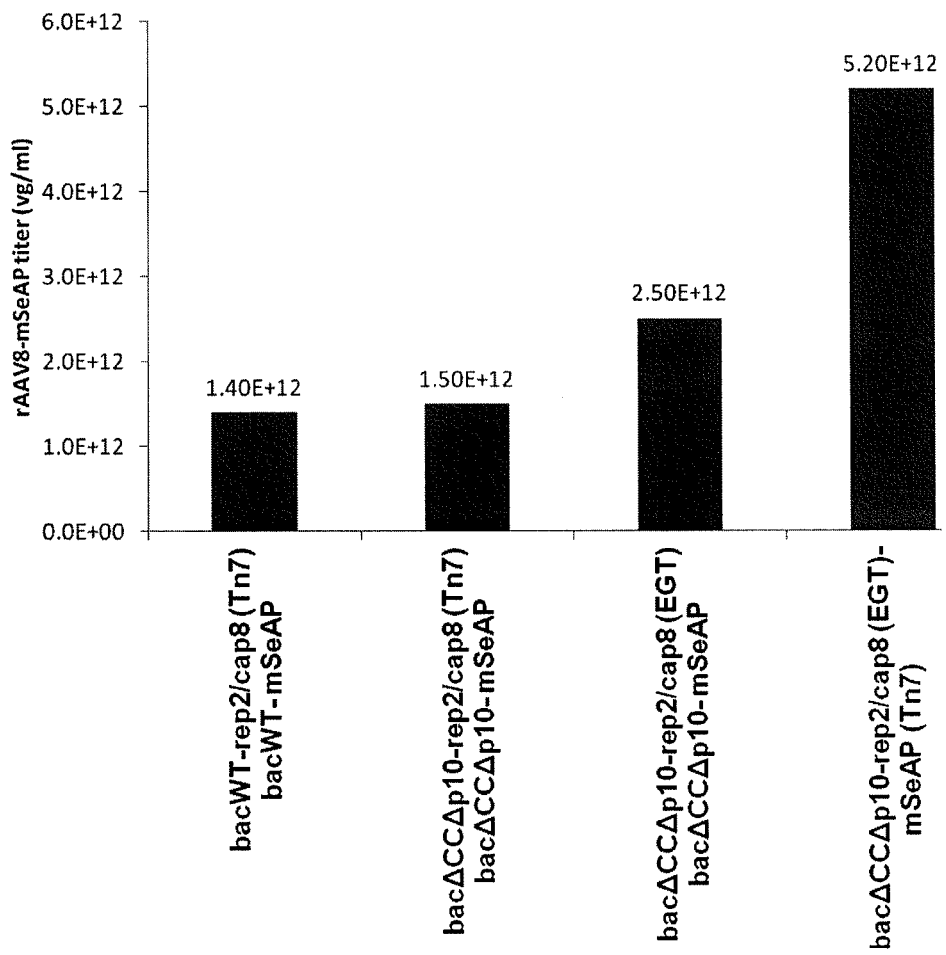

FIG. 5. rAAV productivity after purification by immunoaffinity

The rAAV productivity in the monobac system was evaluated after purification. The results are given as rAAV titer (vg/ml—vector genome/ml).

Figure 6:
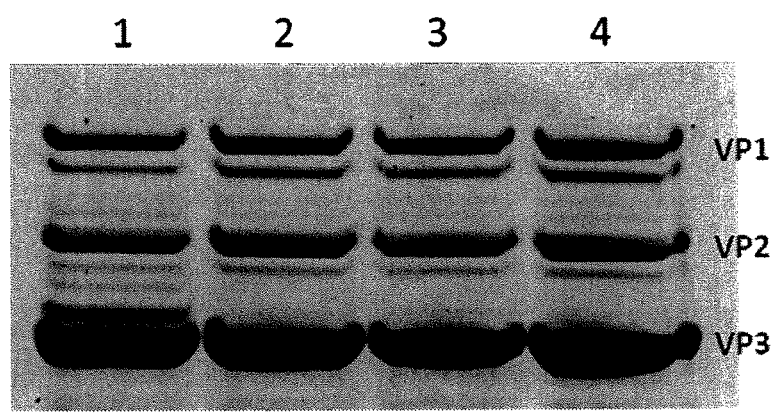

FIG. 6. Protein profile of the purified rAAV vectors

The protein profile of the rAAV vectors was evaluated after purification by immunoaffinity. $5 \times 10^{10}$ vg of rAAV were analyzed by SDS-PAGE and staining of the gel with Coomassie blue.

(1) AAV8-mSeAP produced with the wild-type baculoviruses. $1^{st}$ baculovirus bacWT-rep2/cap8 (Tn7), $2^{nd}$ baculovirus bacWT-mSeAP. (2) AAV8-mSeAP produced with the baculoviruses deleted for the chitinase, cathepsin and p10 genes. $1^{st}$ baculovirus bacΔCCΔp10-rep2/cap8 (Tn7), $2^{nd}$ baculovirus bacΔCCΔp10-mSeAP. (3) AAV8-mSeAP produced with the baculoviruses deleted for the chitinase, cathepsin and p10 genes. $1^{st}$ baculovirus bacΔCCΔp10-rep2/cap8 (EGT), $2^{nd}$ baculovirus bacΔCCΔp10-mSeAP. (4) AAV8-mSeAP produced with the baculovirus deleted for the chitinase, cathepsin and p10 genes. A single baculovirus used, bacΔCCΔp10-rep2/cap8 (EGT)-mSeAP (Tn7).

DETAILED DESCRIPTION OF THE INVENTION

The production of a viral vector, in particular a viral gene therapy vector, requires the expression, in the same cell, of the numerous components of the viral vector. For example, in the case of the production a recombinant AAV in an insect cell, it is necessary to produce, in the cell:

an AAV recombinant genome comprising a 5' ITR (for Inverted Terminal Repeat), and an expression cassette for a heterologous nucleotide sequence of interest (at least one heterologous nucleotide sequence of interest under the control of a promoter which is effective for the expression of said gene in a target cell defined below), and a 3' ITR; and the products of the AAV rep and cap genes.

A baculovirus expression system has been developed in order to facilitate the production of viral vectors, in the sense that a single baculovirus is used to infect the host cells producing the viral vector.

The invention relates in particular to a recombinant baculovirus genome comprising one or more expression cassettes for the protein components required for the production of a heterologous viral vector, and a recombinant genome of a heterologous viral vector (or heterologous genome), said expression cassettes and said heterologous genome being inserted into one or more loci selected from the group consisting of the nonessential genes of the baculovirus which can be replaced with a sequence of interest without modifying the functioning of the baculovirus.

In the context of the present invention, the "nonessential genes of the baculovirus" are defined as genes which can be inactivated or removed from the genome of the baculovirus, without modifying its capacity to grow in insect cell cultures. These genes are genes which are involved specifically in ODV (Occlusion Derived Virus) production or genes which are required for the manipulation of the host insect in the environment, but are not required on the scale of insect cells in culture (Cohen et al. 2009; Virologica Sinica 24: 359-414). According to one particular embodiment, the locus or loci is (are) selected from the group consisting of the polyhedrin, ctx, egt, 39k, orf51, gp37, iap2, p94, p10 and odv-e56 loci, said locus being more particularly the egt locus.

In the context of the invention, the term "heterologous viral vector" is intended to mean a viral vector which is not a baculovirus. The heterologous viral vector may in particular be an adenovirus, an adeno-associated virus, a retrovirus, in particular a lentivirus or a spumavirus, etc. More specifically, the recombinant baculovirus genome according to the invention is capable of being used for the production of viral vectors of any type intended to be used for introducing a heterologous nucleotide sequence into a cell, a tissue or an organism, in particular a viral vector for therapeutic purposes in humans or animals (gene therapy vector).

In the context of the present invention, the term "expression cassette" is intended to mean a combination of elements required for the expression of one or more genes. An expression cassette thus contains a promoter suitable for expression in a host cell, in particular a eukaryotic cell, more particularly an insect cell, and a polyadenylation sequence. Those skilled in the art have several cassettes for expression in eukaryotic cells (in particular insect or mammalian cells) at their disposal.

As mentioned above, the recombinant baculovirus genome according to the invention can be intended for the production of viral vectors of any type, in particular viral gene therapy vectors. For example, the recombinant baculovirus genome can comprise one or more expression cassettes for viral proteins required for the production of an adeno-associated virus, of an adenovirus, of a retrovirus, in particular a lentivirus or a spumavirus, etc. The genes required for the production of such viral particles are well known to those skilled in the art, who will adapt the present recombinant baculovirus genome to the particular viral vector that they wish to produce (Bagnis, Merten, Mezzina (guest editors) 2005: Advanced methods for industrial production, purification, and characterization of gene vectors. Gene Ther 12(S1): 1-177).

According to one preferred embodiment, the recombinant baculovirus genome according to the invention also comprises a viral gene therapy vector recombinant genome, said viral gene therapy vector recombinant genome being inserted into a locus of the baculovirus genome as described above. The viral gene therapy vector recombinant genome inserted into the baculovirus genome will of course depend on the viral gene therapy vector to be ultimately produced. Thus, for the production of an AAV, the viral gene therapy vector recombinant genome will be an AAV recombinant genome comprising a 5' ITR, at least one heterologous nucleotide sequence of interest under the control of a promoter which is effective in the target cell of the recombinant AAV produced, and a 3' ITR. For the production of a lentivirus, the viral gene therapy vector recombinant genome will be a lentivirus recombinant genome comprising a 5' LTR, a major splice donor site, a packaging signal covering the 5' part of the Gag gene, the Rev response element (RRE), the envelope splice acceptor, at least one heterologous nucleotide sequence of interest under the control of a promoter which is effective in the target cell of the recombinant lentivirus produced, and a 3' LTR, in particular a 3' LTR modified with a view to generating SIN (Self-INactivating lentivirus) vectors.

Thus, according to a first variant of the invention, the recombinant baculovirus genome described is a baculovirus genome for the production of an AAV vector.

In this respect, the invention also relates to a recombinant baculovirus genome comprising one or more expression cassettes for the AAV rep and/or cap genes, said one or more expression cassets being inserted into a locus selected from the group consisting of the egt, ctx, 39k, orf51, gp37, iap2, odv-e56, p10 and p94 loci of the baculovirus genome. This recombinant baculovirus genome also preferably contains an AAV recombinant genome in a locus selected from the polyhedrin, egt, ctx, 39k, orf51, gp37, iap2, odv-e56, p10 and p94 loci of the baculovirus genome, said AAV recombinant genome being inserted into a locus different than the locus or loci used for the AAV rep and cap genes.

In one particular embodiment of the first variant, the recombinant baculovirus genome according to the invention comprises at least one expression cassette for the AAV rep and/or cap genes in a locus selected from the group consisting of the nonessential genes of the baculovirus which can be replaced with a sequence of interest without modifying the functioning of the baculovirus. Said at least one expression cassette for the AAV rep and/or cap genes can in particular be included in a locus selected from the group consisting of the polyhedrin, ctx, egt, 39k, orf51, gp37, iap2, p94, p10 and odv-e56 loci, in particular the egt locus.

In another particular embodiment of the first variant, the recombinant baculovirus genome according to the invention also comprises an AAV recombinant genome. The locus for insertion of the AAV recombinant genome is in particular selected from the group consisting of the polyhedrin, egt, ctx, 39k, orf51, gp37, iap2, p94, p10 and odv-e56 loci. According to one particular embodiment, the locus selected for the AAV recombinant genome is a locus different from the locus or loci selected for the expression cassette(s) for rep and/or cap. According to one preferred embodiment, the AVV recombinant genome is inserted into the polyhedrin locus (in particular at the level of the Tn7 recombination site).

According to a first preferred embodiment, the recombinant baculovirus genome according to the invention comprises:
  an AAV recombinant genome in the polyhedrin locus, and
  an expression cassette for the AAV rep/cap genes, in a locus selected from the group consisting of the ctx, egt, 39k, orf51, gp37, iap2, p94, p10 and odv-e56 loci, in particular the egt locus.

According to a second preferred embodiment, the recombinant baculovirus genome according to the invention comprises:
  an AAV recombinant genome in the p94 locus,
  an expression cassette for the AAV rep/cap genes in a locus selected from the group consisting of the polyhedrin, ctx, egt, 39k, orf51, gp37, iap2, p10 and odv-e56 loci, in particular the egt locus.

The expression cassettes for the rep and cap genes are in particular selected according to the gene of interest to express from the recombinant AAV produced and to the type of cells to be transduced with said AAV. Those skilled in the art are able to select and produce the appropriate expression cassettes on the basis of their general knowledge. By way of particular promoters, mention may be made of the early/late baculovirus promoters, such as gp64, or very late baculovirus promoters such as the polyhedrin ($P_{Ph}$) and p10 ($P_{p10}$) gene promoters, if the baculovirus is intended to infect insect cells. The immediate early promoters, such as IE1 (Immediate Early 1), can also be used in the context of the invention, with the possibility of functioning in mammalian cells for example. By way of polyadenylation sequences, mention may in particular be made of the tryptophan hydroxylase (Tph) polyadenylation sequences, or polyadenylation sequences of baculovirus genes.

The rep and cap genes can be selected according to the type of recombinant AAV that it is desired to produce. They can be selected from the rep and cap genes of AAV of any serotype. The rep and cap genes can be included in different expression cassettes or in a single cassette. According to one preferred embodiment, a single expression cassette is used for the expression of the rep and cap genes, According to one embodiment variant, the expression cassette for the AAV rep/cap genes comprises said genes in reverse orientation. These genes in reverse orientation can in particular each be under the control of different promoters, especially different baculovirus promoters, in particular different very late promoters. For example, the very late promoters in question can in particular correspond to the $P_{P10}$ and $P_{Ph}$ baculovirus promoters. According to one particularly preferred embodiment, the expression cassette for rep and cap is produced and inserted into the recombinant baculovirus genome of the invention according to the procedures described in Smith et al., 2009; Mol. Ther. 17: 1888-1896. According to one particular mode, the expression cassette corresponds to that described in the examples below, allowing the expression of the rep2 and cap8 gene products, and therefore the production of recombinant AAV vectors of rAAV8 type, comprising AAV8 capsid proteins, and therefore having the tropism of this particular serotype. This expression cassette is preferentially introduced into the baculovirus genome by transposition, according to procedures well known in the field, in particular using the Bac-to-Bac system sold by the company Invitrogen.

According to one particular embodiment, the expression cassette for the AAV rep/cap genes is inserted into the egt locus, in particular according to the method described in the examples.

The AAV recombinant genome comprises a 5' ITR (for Inverted Terminal Repeat), at least one heterologous nucleotide sequence of interest under the control of a promoter which is effective in the target cell of the recombinant AAV produced, and a 3' ITR. The ITRs can be derived from any AAV serotype known to those skilled in the art.

The term "heterologous nucleotide sequence of interest" is intended to mean a nucleotide sequence which is not a baculovirus gene or an AAV gene and which, when it is expressed in a cell of interest (also termed "target cell"), makes it possible to obtain a desired effect. The heterologous nucleotide sequence may in particular encode a protein, an interfering RNA, an antisense RNA, a microRNA or snRNA. The desired effect can in particular correspond to the expression of the heterologous nucleotide sequence in cells or tissues of a patient. Thus, the heterologous nucleotide sequence can in particular be administered in order to obtain a therapeutic effect. In this respect, the recombinant AAV produced will be usable as a gene therapy vector. The heterologous nucleotide sequence may thus allow the production of a therapeutic protein, for example a protein which is deficient in a diseases, or an interfering RNA in cells requiring reduction of the expression of an abnormal protein, or an snRNA (small nuclear RNA) involved in the removal of a mutated exon responsible for the nonfunctionality of a protein.

The target cell corresponds to any cell in which the expression of the heterologous nucleotide sequence may be of interest, in particular therapeutic interest. The promoter present in the AAV genome will thus be a promoter which allows the expression of the heterologous nucleotide sequence in the target cell. This promoter may be constitutive, inducible or specific for a particular cell or tissue.

Of course, those skilled in the art are familiar with the concepts of gene therapy and will adapt the constituent elements of the present invention to the needs thereof.

The recombinant baculovirus genome can also comprise any AAV sequence which makes it possible to improve the amount or the quality of the recombinant AAV. In this respect, mention may be made of the insertion, into one of the loci mentioned above, of the gene encoding the AAP protein (or Assembly Activating Protein—Sonntag et al., Proc Natl Acad Sci USA. 2010 Jun. 1; 107(22):10220-5).

According to a second variant of the invention, the recombinant baculovirus genome described is a baculovirus genome for the production of a lentiviral vector.

In this respect, the invention also relates to a recombinant baculovirus genome comprising one or more expression cassettes for the gag/pol and rev genes from lentivirus (for example originating from HIV-1) and/or env gene chosen according to the desired tropism, but preferably the G protein originating from the vesicular stomatitis virus (VSV-G), said one or more expression cassettes being inserted into a locus selected from the group consisting of the egt, ctx, 39k, orf51, gp37, iap2, odv-e56, p10 and p94 loci of the baculovirus genome. This recombinant baculovirus genome also preferably contains a lentivirus recombinant genome in a locus selected from the polyhedrin, egt, ctx, 39k, orf51, gp37, iap2, odv-e56, p10 and p94 loci of the baculovirus genome, said lentivirus recombinant genome being inserted into a locus different from the locus or loci used for the lentivirus gag/pol and rev genes and also the env gene.

In one particular embodiment of the first variant, the recombinant baculovirus genome according to the invention comprises at least one expression cassette for the lentivirus gag/pol and rev genes and also the env gene, in a locus selected from the group consisting of the nonessential genes of the baculovirus which can be replaced with a sequence of interest without modifying the functioning of the baculovirus. Said at least one expression cassette for the lentivirus gag/pol and rev genes and also the env gene can in particular be included in a locus selected from the group consisting of the polyhedrin, ctx, egt, 39k, orf51, gp37, iap2, p94, p10 and odv-e56 loci.

In another particular embodiment of the first variant, the recombinant baculovirus genome according to the invention also comprises a lentivirus recombinant genome. The locus for insertion of the lentivirus recombinant genome is in particular selected from the group consisting of the polyhedrin, egt, ctx, 39k, orf51, gp37, iap2, p94, p10 and odv-e56 loci. According to one particular embodiment, the locus chosen for the lentivirus recombinant genome is a locus different than the locus or loci chosen for the expression cassette(s) for gag/pol, rev and/or env. According to one preferred embodiment, the lentivirus recombinant genome is inserted into the polyhedrin locus (in particular at the level of the Tn7 recombination site).

According to a first preferred embodiment, the recombinant baculovirus genome according to the invention comprises:
   a lentivirus recombinant genome in the polyhedrin locus, and
   an expression cassette for the lentivirus gag/pol and rev genes and also the env gene in a locus selected from the group consisting of the ctx, egt, 39k, orf51, gp37, iap2, p94, p10 and odv-e56 loci.

According to a second preferred embodiment, the recombinant baculovirus genome according to the invention comprises:
   a lentivirus recombinant genome in the p94 locus,
   an expression cassette for the lentivirus gag/pol and rev genes and also the env geme in a locus selected from the group consisting of the polyhedrin, ctx, egt, 39k, orf51, gp37, iap2, p10 and odv-e56 loci.

The expression cassettes for the lentivirus gag/pol and rev genes and also the env gene are in particular selected according to the gene of interest to be expressed from the recombinant lentivirus produced and to the type of cells to be tranduced with said lentivirus. Those skilled in the art are able to select and produce the appropriate expression cassettes on the basis of their general knowledge. By way of particular promoters, mention may be made of the early/late baculovirus promoters, such as gp64, or very late baculovirus promoters such as the polyhedrin ($P_{Ph}$) and p10 ($P_{p10}$) gene promoters, if the baculovirus is intended to infect insect cells. The immediate early promoters, such as IE1 (Immediate Early 1) are also usable in the context of the invention, with the possibility of functioning in mammalian cells for example. By way of polyadenylation sequences, mention may in particular be made of the tryptophan hydroxylase (Tph) polyadenylation sequences, or polyadenylation sequences of baculovirus genes.

The term "heterologous nucleotide sequence of interest" is intended to mean a nucleotide sequence which is not a baculovirus gene or a lentivirus gene and which, when it is expressed in a cell of interest (also referred to as "target cell") makes it possible to obtain a desired effect. The heterologous nucleotide sequence can in particular encode a protein, an interfering RNA, an antisense RNA, a microRNA or an snRNA. The desired effect can in particular correspond to the expression of the heterologous nucleotide sequence in cells or tissues of a patient. Thus, the heterologous nucleotide sequence can in particular be administered in order to obtain a therapeutic effect. In this respect, the recombinant lentivirus produced will be usable as a gene therapy vector. The heterologous nucleotide sequence may thus allow the production of a therapeutic protein, for example a protein which is deficient in a disease, or an interfering RNA in cells requiring reduction of the expression of an abnormal protein, or an snRNA (small nuclear RNA) involved in the removal of a mutated exon responsible for the nonfunctionality of a protein.

The target cell corresponds to any cell in which the expression of the heterologous nucleotide sequence may be of interest, in particular therapeutic interest. The promoter present in the lentivirus genome will thus be a promoter which allows the expression of the heterologous nucleotide sequence in the target cell. This promoter may be constitutive, inducible or specific for a particular cell or tissue.

Of course, those skilled in the art are familiar with the concepts of gene therapy and will adapt the constituent elements of the present invention to the needs thereof.

The recombinant baculovirus genome may be derived from any baculovirus comprising the polyhedrin locus (or equivalent), and at least one or more of the other loci mentioned above (or one or more equivalent loci).

According to one particular embodiment, the recombinant baculovirus genome according to the invention is a bacmid. In the context of the present invention, a "bacmid" is a baculovirus genome comprising genetic elements for maintaining and amplifying a baculovirus genome in a prokaryotic cell. It may in particular comprise a bacterial origin of replication, a selectable gene, in particular a gene for resistance to an antibiotic such as kanamycin, and a recombination cloning site such as "Tn7", which are inserted into a baculovirus locus, such as the polyhedrin locus. According to one variant, the recombinant bacmid according to the invention comprises an origin of replication, a kanamycin resistance gene and a Tn7 recombination cloning site in the polyhedrin locus (in particular the AcMNPV bacmid described in Luckow et al., 1993; J. Virol. 67:4566-4579).

Thus, the recombinant baculovirus genome can correspond to a sequence capable of replicating in insect cells and in a prokaryotic organism such as *E. coli*. In particular, any baculovirus genome comprising a DNA construct which allows the genome to be maintained in a prokaryotic organism, in particular a BAC replicon, can be used. According to one preferred aspect, the baculovirus genome of the invention is derived from an AcMNPV or SpliNPV backbone. The position of the ctx, egt, 39k, orf51, gp37, iap2 and odv-e56 genetic loci in the AcMNPV reference sequence (accession number NC001623) are in particular described in Table 1 of international application WO 2010/055292. With regard to the p94 and p10 genetic loci, their position is shown in FIG. 1 (AcMNPV reference sequence—accession number NC001623).

According to one particular embodiment, the recombinant baculovirus genome is derived from AcMNPV and comprises a deletion of the chitinase, cathepsin and p10 genes. Thus, according to this embodiment, the invention relates to a recombinant AcMNPV baculovirus genome devoid of the chitinase, cathepsin and p10 genes and comprising an expression cassette for the AAV rep/cap genes in a locus selected from the group consisting of the egt, polyhedrin, ctx, 39k, orf51, gp37, iap2 and odv-e56, p10 and p94 loci, in particular the egt locus.

In one variant of this embodiment, the bacmid comprises, moreover, an AAV recombinant genome in the polyhedrin locus (Tn7 of the bacmid).

In another variant of this embodiment, the baculovirus genome comprises, moreover, an AAV recombinant genome in the p94 locus.

The deletion of the chitinase, cathepsin and p10 genes in the baculovirus backbone allows a highly efficient production of AAV vectors, enabling reduced proteolytic degradation, in particular of the VP1 and VP2 proteins, and thus an increase in the infectivity and the effectiveness in vivo. The deletion of these genes can be carried out according to any procedure known to those skilled in the art. Use will more particularly be made of the method described in the examples implementing the homologous recombination process (Datsenko and Wanner, 2000; Proc Natl Acad Sci USA. 97(12):6640-6645) in *E. coli* bacteria containing the bacmid to be modified (in particular the AcMNPV bacmid described in Luckow et al., 1993; J. Virol. 67:4566-4579).

According to one particular embodiment, the chi/v-cath genes (nucleotides 105282-107954 according to the genetic map of AcMNPV (Ayres et al., 1994)) and p10 (nucleotides 118839-119121) gene are deleted.

According to one variant of the embodiment comprising a deletion of the chitinase, cathepsin and p10 genes, the deletion of the p10 gene is not accompanied by a deletion of the promoter of the p10 gene. In other words, the recombinant baculovirus genome deficient for the chitinase, cathepsin and p10 genes comprises a functional $P_{P10}$ promoter (corresponding to the nucleotides 118739-118836 of the genetic map of AcMNPV).

According to another variant of the embodiment comprising a deletion of the chitinase, cathepsin and p10 genes, the deletion of the p10 gene is accompanied by a deletion of the adjacent p26 and p74 genes. According to one particular aspect of this embodiment, the deletion of the p26, p10 and p74 genes corresponds to nucleotides 118044-121072 of the genetic map of AcMNPV (Ayres et al., 1994).

According to a second aspect, the invention relates to a recombinant baculovirus comprising a genome corresponding to the baculovirus genome described above. According to one preferred embodiment, the recombinant baculovirus comprises a genome corresponding to the recombinant bacmid described above.

According to a third aspect, the invention relates to a method for producing a baculovirus according to the invention, comprising culturing a prokaryotic cell containing the recombinant bacmid defined above under conditions suitable for the production of a baculovirus. These conditions are well known to those skilled in the art (Smith et al., 2009, above; Luckow et al., 1993, above).

According to a fourth aspect, the invention relates to a eukaryotic or prokaryotic cell containing the baculovirus genome defined above. The cell may in particular be a mammalian or insect eukaryotic cell, in particular an insect cell which has been infected with a recombinant baculovirus as defined above.

Among the insect cells, preference will be given to those derived from the *Spodoptera frugiperda* or *Trichoplusia ni* lines, for example the Sf21, Sf9, High Five or TN 5B1-4 cells. Among the mammalian cells, mention may in particular be made of the HEK293 line, which is known to be capable of being infected with a baculovirus. In the latter case, the promoter(s) present in the expression cassette for the rep and cap genes will be suitable for expression in mammalian cells. Mention may in particular be made of the CMV promoter and other promoters well known in the field.

According to a fifth aspect, the invention relates, moreover, to a method for producing a viral vector, in particular a viral gene therapy vector, comprising culturing the recombinant baculovirus as defined above with a cell, in particular an insect cell or a mammalian cell, under conditions which allow the infection of the cell with the baculovirus and the production of said viral vector.

With regard to the production of enveloped vectors (such as retroviral vectors), this involves a mammalian cell (for example an HEK293 cell).

According to one particular embodiment, the method according to the invention is a method for producing a recombinant AAV comprising culturing the recombinant baculovirus defined above with a cell, in particular an insect cell (e.g. an Sf21, Sf9, High Five or TN 5B1-4 cell), capable of being infected with said baculovirus, under conditions which allow the infection of the cell with the baculovirus and the production of said recombinant AAV. Thus, it is possible to produce a recombinant AAV from an infection with a single baculovirus. Particular, nonlimiting, conditions for producing a recombinant AAV according to the invention are in particular described in the examples. Of course, those skilled in the art are able to adapt these production conditions on the basis of their general knowledge (Smith et al., above).

By virtue of this method, a recombinant AAV production is obtained which is at least 5 times greater than that obtained with a system requiring infection with two baculoviruses, such as the system described by Smith et al.

According to another particular embodiment, the method according to the invention is a method for producing a recombinant lentivirus, comprising culturing the recombinant baculovirus as defined above with a mammalian cell (for example an HEK293 cell) capable of being infected with said baculovirus, under conditions which allow the infection of the cell with the baculovirus and the production of said recombinant lentivirus.

The examples below are provided in order to illustrate the invention.

Examples

Materials and Methods

Sequences

TABLE 1 primer sequences

| Primer | Sequence 5' to 3' | Use* |
|---|---|---|
| EGT-lox-F | TTACGGTCGTCAAGCCCAAACTGTTTGCGTATTCAACTAAAACTTATTGCG GTAATATCACTACCGTTCGTATAGCATACATTATACGAAGTTATAATAGG AACTTCATTTAAATGGCGC (SEQ ID No. 1) | insertion of rep2/cap8 into the AcMNPV bacmid at the level of the EGT locus (11634-12486) |
| EGT-SV40-R | TCCCGGCTTCCAAGGCCTCGTCGCTCGATTGTAGTCCGCCTTGCGTAATAA ACGCCGCCATTTTTTTATGACGCAGCACGG CAGACATGATAAGATACATTGATGAGTTTG (SEQ ID No. 2) | insertion of rep2/cap8 into the AcMNPV bacmid at the level of the EGT locus (11634-12486) |
| EGT-Control 150F | ATGACTATTCTCTGCTGGC (SEQ ID No. 3) | verification |
| EGT-Control 150R | ATTGGCCGTGTTTCCTAC (SEQ ID No. 4) | verification |
| M13 PUC F | CCAGTCACGACGTTGTAAAACG (SEQ ID No. 5) | verification of the bacmids transposed |
| M13 PUC R | AGCGGATAACAATTTCACACAGG (SEQ ID No. 6) | verification of the bacmids transposed |
| Genta | AGCCACCTACTCCCAACATC (SEQ ID No. 7) | verification of the bacmids transposed |
| CC-KO-F | CCGCTGTTGAAACAATATTTTATAATACCCTGTTTATAGTTAACAATGTCG GCAGCGTCTATGGCCATAGGAATAGGGCCTACCGTTCGTATAATGTATGC TATACGAAGTTAT (SEQ ID No. 8) | inactivation of the chitinase/cathepsin genes nt 105771-107700 |

TABLE 1-continued primer sequences

| Primer | Sequence 5' to 3' | Use* |
|---|---|---|
| CC-KO-R | CCGCTGTTGAAACAATATTTTATAATACCCTGTTTATAGTTAACAATGTCG GCAGCGTCTATGGCCATAGGAATAGGGCCTACCGTTCGTATAATGTATGC TATACGAAGTTAT (SEQ ID No. 9) | inactivation of the chitinase/cathepsin genes nt 105771-107700 |
| chitinase-105625F | CGCGGCCGTACATGGCGACGCCCA (SEQ ID No. 10) | verification |
| cathepsin-107849R | GTTTTTAAAGGTCCAATATGGAATG (SEQ ID No. 11) | verification |
| p10-KO-F | TTGTATATTAATTAAAATACTATACTGTAAATTACATTTTATITACAATCT ACCGTTCGTATAGCATACATTATACGAAGTTAT (SEQ ID No. 12) | inactivation of the p10 encoding sequence (from the start codon to the stop codon) nt 118839-119121 |
| P10-KO-R | GAATCGTACGAATATTATAAAACAATTGATTTGTTATTTTAAAAACGATTT ACCGTTCGTATAATGTATGCTATACGAAGTTAT (SEQ ID No. 13) | inactivation of the p10 encoding sequence (from the start codon to the stop codon) nt 118839-119121 |
| p10-118725-F | CCGGGACCTTTAATTCAACCCAACA (SEQ ID No. 14) | verification |
| p10-119259-R | CAGCATTTGTTATACACACAGAACT (SEQ ID No. 15) | verification |

*numbering according to Ayres et al., Virology. 1994 Aug. 1; 202(2):586-605.

Baculovirus Gene Deletion

The deletion of cathepsin and of chitinase in the wild-type AcMNPV bacmid was carried out using the E. coli DH10Bac strain containing the AcMNPV bacmid (Luckow et al., 1993, cf above) and transformed with pKD46 (Datsenko and Wanner, 2000, PNAS Vol 97 (12) pages 6640-6645). A PCR product necessary for the inactivation of the cathepsin/chitinase genes was generated by means of the CC-KO-F and CC-KO-R primers (table 1). The inactivation of the genes was carried out according to the method described by Marek et al., 2011 and evaluated using the chitinase-105625F and cathepsin-107849R primers (table 1). The suppression of the CAT marker gene of the cathepsin/chitinase null bacmid (AcbacΔCCΔcat) was carried out according to the method described by Marek et al. (Marek et al., 2011, Biotechnol Bioeng, Vol 108 (5) pages 1056-67) and verified by PCR and sequencing, using the primers mentioned above. The inactivation of the p10 coding sequence in AcbacΔCCΔcat was carried out in the same way, with a PCR product being generated with the p10-KO-F/p10-KO-R primers (table 1). The verification of the correct inactivation of the gene was carried out by PCR and sequencing with the pair of primers p10-118725-F/p10-119259-R (table 1). The final gene inactivation allows the production of the cathepsin/chitinase/p10 null bacmid (AcbacΔCCΔp10).

Insertion of the Rep2/Cap8 Cassette at the egt Locus of the AcMNPV Bacmid

The insertion of the expression cassette for the AAV rep2 and cap8 genes at the egt locus was carried out in the genome of the bacmid, already inactivated for the chitinase, cathepsin and p10 genes.

The rep2/cap8 expression cassette was amplified by PCR from the pSR660 plasmid, by virtue of the EGT-lox-F and EGT-SV40-R primers. The insertion of this PCR product into the genome of the bacmid was carried out according to the method described by Marek et al., 2011. Briefly, the rep2/cap8 expression cassette was coupled to a gene for resistance to the antibiotic chloramphenicol, bordered by the lox66 and lox71 sequences (Suzuki et al., 2005; appl Environ Microbiol. 71(12) 8472-8480). These two genetic elements make it possible to subsequently remove this resistance gene, by the action of the Cre recombinase, which can then be used for successive series of deletions or insertions of genes in the genome of the bacmid. The cassette described above is then amplified by PCR by virtue of the EGT-lox-F and EGT-SV40-R primers. This PCR product is purified on agarose gel and treated with the DpnI restriction enzyme. It is then used to chemically transform competent bacteria containing the bacmid, already inactivated for the chitinase, cathepsin and p10 genes, the pKD46 plasmid (Datsenko and Wanner 2000). The expression of the lambda phase Red operon genes encoded by the pKD46 plasmid is induced by adding L-arabinose at 0.1% (weight/volume). The chloramphenicol-resistant recombinant bacteria are analyzed by PCR in order to verify the insertion of the rep2/cap8 expression cassette into the genome of the bacmid already inactivated for the chitinase, cathepsin and p10 genes, at the egt locus, using the EGT-Control 150F and EGT-Control 150R primers (table 1). This insertion made it possible to obtain the Monobac-AcbacΔCCΔp10-rep2cap8(EGT) bacmid.

Insertion of the rep2/cap8 Cassette and of the Recombinant Genome of rAAV into the Bacmid at the Tn7 Site E. coli DH10b bacteria containing either the AcbacΔCCΔp10 bacmid or the Monobac-AcbacΔCCΔp10-rep2cap8(EGT) bacmid were transformed with the pMON7124 plasmid (Luckow et al., 1993). Either the AAV recombinant genome encoding the murine secreted alkaline phosphatase (mSeAP) reporter gene under the control of the CMV promoter and surrounded by the AAV ITRs, or the expression cassette for the AAV rep2 and cap8 genes, was inserted by recombination (Luckow et al., 1993) into these bacteria, and also into DH10bac bacteria containing the wild-type Acbac bacmid (Luckow et al. 1993). These recombinations were respectively carried out using the pFBD-mSeAP and pFBD-SR660 plasmids. These recombinations made it possible to generate the bacmids:

AcbacWT-rep2/cap8(Tn7); AcbacΔCCΔp10-rep2/cap8 (Tn7) allowing the expression of the rep2 and cap8 genes from the Tn7 site.

AcbacWT-mSeAP(Tn7); AcbacΔCCΔp10-mSeAP(Tn7) containing the rAAV genome encoding the mSeAP gene, at the Tn7 site of the bacmid.

AcbacΔCCΔp10-rep2/cap8(EGT)mSeAP(Tn7) allowing the expression of the rep2 and cap8 genes from the egt locus and containing the rAAV genome encoding the mSeAP gene at the Tn7 site of the bacmid.

Finally, the AcbacΔCCΔp10-rep2/cap8(EGT) bacmid allows the expression of the rep2 and cap8 genes from the egt locus, but has not received the recombinant genome of rAAV-mSeAP at the Tn7 site.

Cell Line, Baculovirus and rAAV Production

The Sf9 cells are maintained at 27° C. in SF900II medium (Invitrogen) in one-liter Bellco spinners. The baculoviruses are generated according to the Bac-to-Bac protocol from Invitrogen, and then amplified in Sf9 cell suspension cultures, in 100 ml Bellco spinners. To produce the rAAV vectors, the Sf9 cells are infected with one or two baculovirus(es) encoding the AAV rep2 and cap8 genes and containing the mSeAP cassette of the rAAV genome. 70 ml of Sf9 cells at a density of $10^6$ cell/ml are thus infected with an MOI of 0.1 in order to produce the rAAV vectors. 96 hours after the production, an aliquot is removed in order to carry out titrations of the rAAV vectors, the rest is stored at −80° C.

rAAV Vector Purification and Characterization

The rAAV vectors are purified from the whole cell culture on an AVB sepharose immunoaffinity column (GE Healthcare) according to the recommendations of Smith et al., 2009. The purified rAAV vectors are analyzed ($5\times10^{+10}$ vg) on an "SDS-PAGE" polyacrylamide gel (NuPAGe system, Invitrogen). After migration, the gel is stained with coomassie blue.

Determination of the rAAV Vector Viral Genome Titers

In order to determine the titer in terms of viral genomes (vg) of the rAAV vectors produced, a viral DNA extraction is carried out directly from the whole of the cell culture, or else from purified rAAV vector samples. This extraction is carried out using the MagNA Pure DNA and viral NA small volume kit system (MagNA Pure 96, Roche). A real-time quantitative PCR is then carried out, with primers which hybridize the ITRs of the AAV. The absolute quantification is carried out relative to a reference plasmid which contains the regions amplified by quantitative PCR and the number of copies of which is known. The titrations are carried out at the same time, on the same plate and under the same conditions and by an independent operator, in order to reduce the experimental variability as much as possible.

Protein Detection by Western Blot

The samples of culture containing the rAAV vector or purified samples are analyzed by Western blot in order to detect the presence of the VP proteins and of the Rep proteins of AAV. The proteins are visualized according to the method developed by LI-COR, with an Odyssey apparatus and the Odyssey 2.1 software. The primary antibodies used are mouse anti-VP IgG1 clone B1 (Progen) for detection of the VP proteins and mouse anti-Rep IgG1 clone 303.9 (Progen) for detection of the Rep proteins. These antibodies are used respectively at a $\frac{1}{250}^{th}$ and $\frac{1}{100}^{th}$ dilution in infrared imaging system blocking buffer, LI-COR. The goat secondary antibodies used are directed against the primary antibodies and coupled to the "Dye 680" fluorochrome from LI-COR. The P35 baculovirus protein is also detected using a specific primary antibody and a secondary antibody coupled to "Dye 800" from LI-COR.

Statistical Analysis

The statistical significance of the differences observed for the titers of rAAV obtained during the production was analyzed. A Fisher test was carried out in order to determine the equality of two variances. A Student's test was subsequently performed. The Excel software was used for these analyses.

Results

Generation of a Baculovirus Expressing, at the egt Locus, the AAV rep2 and cap8 Genes An already modified bacmid genome was used to insert the AAV rep2 and cap8 genes into the genome of the AcMNPV bacmid. We previously showed that the use of a bacmid inactivated for the chitinase, cathepsin and p10 genes reduced the proteolysis of the rAAV capsid for certain serotypes. The insertion of the AAV rep2 and cap8 genes at the egt locus was thus carried out in the AcbacΔCCΔp10 bacmid, according to the methodology developed by Marek et al., 2011 (FIG. 1). This insertion was verified by PCR and sequencing. It resulted in the creation of the AcbacΔCCΔp10-rep2cap8(EGT) bacmid. This bacmid still has the conventional recombination cloning site, Tn7 (Luckow et al., 1993), into which the rAAV genome expressing the mSeAP gene could be inserted, thus generating the AcbacΔCCΔp10-rep2cap8(EGT)SeAP(Tn7) construct.

In parallel, the control bacmids were generated with the insertion at the Tn7 site of the rAAV genome or of the expression cassette for the AAV rep2 and cap8 genes. These control bacmids were generated on an unmodified genetic background or on the genetic background inactivated for the chitinase, cathepsin and p10 genes.

After recombination, the bacmid DNAs were extracted and purified according to the Bac-to-Bac protocol (Invitrogen) and the absence of nonrecombinant bacmid was verified by PCR. The bacmids were transfected into Sf9 cells, plate-purified by lysis plaque and amplified. No difference in terms of baculovirus titer (pfu/ml) was observed between all the constructs.

Insertion of the AAV rep2 and cap8 Genes at the Egt Locus Allows Expression of Said Genes First of all, the capacity to generate the AcbacΔCCΔp10-rep2cap8(EGT) baculovirus in Sf9 cells, without modifying the viral titer, confirms the possibility of inserting a gene expression cassette at the egt locus without modifying the viability of the baculovirus, as previously observed by Noad et al., 2009.

The protein expression level can be modified according to the site of insertion of the gene into the baculovirus genome (Noad et al., 2009). The egt locus was thus chosen for inserting the rep2/cap8 expression cassette on the basis of an equivalence of expression in comparison with the expression directed from the Tn7 site (Noad and al.).

As observed in FIG. 2, the AAV Rep and VP proteins are expressed at comparable levels, whether the expression cassette is inserted at the egt locus as in the AcbacΔCCΔp10-rep2cap8(EGT) construct (FIG. 2, MB C1 and C2) or at the Tn7 site for the AcbacΔCCΔp10 and AcbacWT constructs (FIG. 2, ΔCCP-SR660 C1 and C2; WT-SR660 C1 and C2).

After insertion of the rAAV mSeAP genome at the Tn7 site of the bacmid (AcbacΔCCΔp10-rep2cap8(EGT)SeAP (Tn7)), the expression of the rep2 and cap8 genes remains equivalent to that observed for this same baculovirus not containing the rAAV genome (FIG. 3).

rAAV Production by a Single Baculovirus Improves Cell Productivity rAAV productions were carried out in spinners under identical conditions. The rAAV titers were then determined and are indicated in FIG. 4. Conventional production with 2 baculoviruses (Smith et al., 2009) using the AcbacWT-rep2/cap8(Tn7) and AcbacWT-mSeAP(Tn7) baculoviruses makes it possible to obtain a titer of $1.44 \times 10^{10}$ vg/ml of rAAV. The equivalent production using this time the baculoviruses inactivated for the chitinase, cathepsin and p10 genes, AcbacΔCCΔp10-rep2/cap8(Tn7) and AcbacΔCCΔp10-mSeAP(Tn7) makes it possible to obtain titers of $2.23 \times 10^{10}$ vg/ml. These results are in the same order of magnitude as those obtained for productions carried out with the unmodified bacmid genome. In order to verify the locus effect of moving the rep2/cap8 expression cassette from the Tn7 site to the egt locus, productions were carried out with the AcbacΔCCΔp10-rep2/cap8(EGT) baculovirus and the AcbacΔCCΔp10-mSeAP(Tn7) baculovirus. The titer obtained is $4.63 \times 10^{10}$ vg/ml of rAAV, i.e. double the titer obtained in comparison with the productions where the rep2/cap8 cassette is inserted at the Tn7 site ($p=0.005$). This result shows a positive locus effect for the production of rAAV when the rep2/cap8 expression cassette is inserted at the egt locus instead of the Tn7 site. Finally, rAAV production using a single baculovirus, AcbacΔCCΔp10-rep2/cap8(EGT)-mSeAP(Tn7), resulted in $9.4 \times 10^{10}$ vg/ml, thus enabling an increase by a factor 6.5 ($p=0.006$) in productivity compared with the rAAV production carried out with two baculoviruses AcbacWT-rep2/cap8(Tn7) and AcbacWT-mSeAP(Tn7). After purification of the vectors produced, a 4-fold gain is still found in favor of the rAAV production carried out with a single baculovirus, AcbacΔCCΔp10-rep2/cap8(EGT)-mSeAP(Tn7), in comparison with the rAAV production carried out with two baculoviruses AcbacWT-rep2/cap8(Tn7) and AcbacWT-mSeAP(Tn7) (FIG. 6).

Moreover, the analysis of the protein profile of the recombinant AAV vectors purified shows a disappearance of recombinant AAV capsid degradation bands associated with the activity of the baculovirus cathepsin (FIG. 6). These bands are visible for the AAV vectors produced with the wild-type baculovirus (FIG. 6, lane 1). These degradation bands are no longer present in the recombinant AAV vectors produced with the baculoviruses for which the chitinase, cathepsin and p10 genes are removed from the baculovirus genome (FIG. 6, lanes 2; 3; 4). This reduction in the degradation of the recombinant AAV vectors is associated with an increase in in vivo infectivity for these vectors.

The invention claimed is:

1. A recombinant baculovirus genome comprising:
   (i) one or more expression cassettes comprising adeno-associated virus (AAV) rep and cap genes under the control of a very late promoter suitable for expression of said genes in an insect host cell, and
   (ii) a recombinant genome of an AAV vector,
   wherein said one or more expression cassettes is(are) inserted into the egt locus;
   wherein said recombinant genome of an AAV vector is inserted into the polyhedrin locus; and
   wherein the chitinase, cathepsin and p10 genes are deleted.

2. The recombinant baculovirus genome as claimed in claim 1, said rep and cap genes being contained in a single expression cassette.

3. The recombinant baculovirus genome as claimed in claim 1, said baculovirus genome being derived from AcMNPV.

4. The recombinant baculovirus genome as claimed in claim 1, wherein the AAV recombinant genome comprises a heterologous gene encoding a protein, an interfering RNA or an antisense RNA, which is therapeutic.

5. The recombinant baculovirus genome as claimed in claim 1, said recombinant baculovirus genome being a bacmid.

6. A recombinant baculovirus containing a recombinant baculovirus genome as claimed in claim 1.

7. A eukaryotic or prokaryotic cell containing the recombinant baculovirus genome as claimed in claim 1.

8. The cell as claimed in claim 7, said cell being an insect cell derived from the *Spodoptera frugiperda* or *Trichoplusia ni* lines.

9. A method for producing a recombinant virus comprising culturing a cell with one or more recombinant baculovirus as claimed in claim 6 under conditions which allow the infection of the cell with the baculovirus and the production of said recombinant virus.

10. A eukaryotic cell infected with the recombinant baculovirus of claim 6.

11. The cell as claimed in claim 7, said cell being selected from the group consisting of Sf21, Sf9, TN 5B1-4 and High Five cells.

12. The cell as claimed in claim 10, said cell being an insect cell derived from the *Spodoptera frugiperda* or *Trichoplusia ni* lines.

13. The cell as claimed in claim 10, said cell being selected from the group consisting of SF21, SF9, TN 5B1-4 and High Five cells.

14. A recombinant baculovirus genome comprising:
   (i) one or more expression cassettes comprising adeno-associated virus (AAV) rep and cap genes under the control of a very late promoter suitable for expression of said genes in an insect host cell, and
   (ii) a recombinant genome of an AAV vector,
   wherein said one or more expression cassettes is(are) inserted into the egt locus; and
   wherein said recombinant genome of an AAV vector is inserted into the polyhedrin locus.

* * * * *

UNITED STATES PATENT AND TRADEMARK OFFICE
CERTIFICATE OF CORRECTION

PATENT NO.         : 10,017,783 B2
APPLICATION NO.    : 14/234988
DATED              : July 10, 2018
INVENTOR(S)        : Lionel Galibert, Otto-Wilhelm Merten and Aurélien Jacob It is certified that error appears in the above-identified patent and that said Letters Patent is hereby corrected as shown below:

In the Specification

Columns 13-14,
Line 15, Primer Row p10-KO-F,
"TTGTATATTAATTAAAATACTATACTGTAAATTACATTTTATITACAATCT" should read
--TTGTATATTAATTAAAATACTATACTGTAAATTACATTTTATTTACAATCT--.

Signed and Sealed this
Third Day of September, 2019

Andrei Iancu
*Director of the United States Patent and Trademark Office*

SEQUENCE LISTING

```
<160> NUMBER OF SEQ ID NOS: 15

<210> SEQ ID NO 1
<211> LENGTH: 120
<212> TYPE: DNA
<213> ORGANISM: Artificial
<220> FEATURE:
<223> OTHER INFORMATION: primer

<400> SEQUENCE: 1
ttacggtcgt caagcccaaa ctgtttgcgt attcaactaa aacttattgc ggtaatatca      60
ctaccgttcg tatagcatac attatacgaa gttataatag gaacttcatt taaatggcgc     120

<210> SEQ ID NO 2
<211> LENGTH: 111
<212> TYPE: DNA
<213> ORGANISM: Artificial
<220> FEATURE:
<223> OTHER INFORMATION: primer

<400> SEQUENCE: 2
tcccggcttc caaggcctcg tcgctcgatt gtagtccgcc ttgcgtaata aacgccgcca      60 ttttttatg acgcagcacg gcagacatga taagatacat tgatgagttt g              111

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
atgactattc tctgctggc                                                   19

<210> SEQ ID NO 4
<211> LENGTH: 18
<212> TYPE: DNA
<213> ORGANISM: Artificial
```

```
<220> FEATURE:
<223> OTHER INFORMATION: primer

<400> SEQUENCE: 4
attggccgtg tttcctac                                                    18

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ccagtcacga cgttgtaaaa cg                                               22

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
agcggataac aatttcacac agg                                              23

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
agccacctac tcccaacatc                                                  20

<210> SEQ ID NO 8
<211> LENGTH: 114
<212> TYPE: DNA
<213> ORGANISM: Artificial
<220> FEATURE:
<223> OTHER INFORMATION: primer

<400> SEQUENCE: 8
ccgctgttga aacaatattt tataataccc tgtttatagt taacaatgtc ggcagcgtct      60
atggccatag gaatagggcc taccgttcgt ataatgtatg ctatacgaag ttat           114

<210> SEQ ID NO 9
<211> LENGTH: 114
<212> TYPE: DNA
<213> ORGANISM: Artificial
<220> FEATURE:
<223> OTHER INFORMATION: primer

<400> SEQUENCE: 9
ccgctgttga aacaatattt tataataccc tgtttatagt taacaatgtc ggcagcgtct      60
atggccatag gaatagggcc taccgttcgt ataatgtatg ctatacgaag ttat           114

<210> SEQ ID NO 10
<211> LENGTH: 24
<212> TYPE: DNA
<213> ORGANISM: Artificial
```

```
<220> FEATURE:
<223> OTHER INFORMATION: primer

<400> SEQUENCE: 10
cgcggccgta catggcgacg ccca                                          24

<210> SEQ ID NO 11
<211> LENGTH: 25
<212> TYPE: DNA
<213> ORGANISM: Artificial
<220> FEATURE:
<223> OTHER INFORMATION: primer

<400> SEQUENCE: 11
gtttttaaag gtccaatatg gaatg                                         25

<210> SEQ ID NO 12
<211> LENGTH: 84
<212> TYPE: DNA
<213> ORGANISM: Artificial
<220> FEATURE:
<223> OTHER INFORMATION: primer

<400> SEQUENCE: 12
ttgtatatta attaaaatac tatactgtaa attacatttt atttacaatc taccgttcgt   60
atagcataca ttatacgaag ttat                                          84

<210> SEQ ID NO 13
<211> LENGTH: 84
<212> TYPE: DNA
<213> ORGANISM: Artificial
<220> FEATURE:
<223> OTHER INFORMATION: primer

<400> SEQUENCE: 13
gaatcgtacg aatattataa aacaattgat ttgttatttt aaaaacgatt taccgttcgt   60
ataatgtatg ctatacgaag ttat                                          84

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
ccgggacctt taattcaacc caaca                                         25

<210> SEQ ID NO 15
<211> LENGTH: 25
<212> TYPE: DNA
<213> ORGANISM: Artificial
<220> FEATURE:
<223> OTHER INFORMATION: primer

<400> SEQUENCE: 15
cagcatttgt tatacacaca gaact                                         25
```